United States Patent
Ikuno

[11] 3,980,085
[45] Sept. 14, 1976

[54] HIGH FREQUENCY APPARATUS FOR HEAT TREATMENT OF BIOLOGICAL TISSUE

[75] Inventor: Yuji Ikuno, Fuchu, Japan

[73] Assignee: Olympus Optical Co., Ltd., Tokyo, Japan

[22] Filed: June 10, 1975

[21] Appl. No.: 585,769

[30] Foreign Application Priority Data
June 17, 1974 Japan................................ 49-68998

[52] U.S. Cl. .................... 128/303.17; 128/422
[51] Int. Cl.² ........................................ A61N 3/04
[58] Field of Search................. 128/303.13, 303.14, 128/303.17, 303.18, 422

[56] References Cited
UNITED STATES PATENTS

| | | | |
|---|---|---|---|
| 2,444,173 | 6/1948 | St. Pierre | 128/303.18 |
| 3,634,652 | 1/1972 | Shimizu et al. | 128/303.18 |
| 3,675,655 | 7/1972 | Sittner | 128/303.17 |
| 3,885,569 | 5/1975 | Judson | 128/303.14 |

FOREIGN PATENTS OR APPLICATIONS

| | | | |
|---|---|---|---|
| 1,215,305 | 4/1960 | France | 128/303.17 |

OTHER PUBLICATIONS

Honis, "Mechanism of Cutting in Electrosurgery", IEEE Trans. on Bio-Hed. Ens., Jan. 1975, pp. 58–62.

*Primary Examiner*—Robert W. Michell
*Assistant Examiner*—Lee S. Cohen
*Attorney, Agent, or Firm*—Ostrolenk, Faber, Gerb & Soffen

[57] ABSTRACT

The apparatus comprises a high frequency oscillator, an amplifier, and a pair of electrodes for treatment of a biological tissue. A high frequency voltage of constant magnitude is applied across the electrodes to permit a current flow across a biological tissue which is held between the electrodes, thereby causing Joule's heat to be produced depending upon the resistance thereof for the purpose of coagulation, excision or erasion of the biological tissue.

4 Claims, 4 Drawing Figures

HIGH FREQUENCY APPARATUS FOR HEAT TREATMENT OF BIOLOGICAL TISSUE

BACKGROUND OF THE INVENTION

The invention relates to a high frequency apparatus for heat treatment of a biological tissue.

High frequency apparatus is already known which effects the excision or coagulation of a biological tissue or lymph to stop the hemorrhage by passing a high frequency current having a frequency on the order of several hundreds kHZ to several MHz through a biological tissue such as the stomach, intestines, liver or the like so that Joule's heat may be produced by the electrical resistance which the tissue presents and the current flow therethrough. In a conventional high frequency apparatus of this kind, the load characteristic defining the relationship between a load current which passes through the tissue to be treated and the voltage applied across electrodes which are directly applied against the tissue is chosen to exhibit a constant voltage characteristic, with a no-load voltage in excess of 1000 volts peak-to-peak. When such high frequency apparatus is used in combination with so-called bipolar electrodes for the purpose of coagulation, an inconvenience is caused in that during the energization, a spark discharge may be produced between the tissue and the electrode when the electrical resistance of the tissue engaged by the electrode increases as a result of a change in its composition. The discharge will be initiated at that electrode having a greater contact resistance with the tissue than the other, and in the region of discharge, the potential gradient will be substantially increased as compared with that in the region of the other electrode, whereby the generation of heat will be concentrated only in the region of the first mentioned electrode, resulting in a coagulation of only that portion of the tissue which is located adjacent thereto. In this manner, it has been difficult heretofore to achieve a uniform coagulation of the tissue located across the pair of electrodes. Such failure is liable to occur when the electrodes are spaced apart over an increased distance in order to achieve a coagulation over an extensive area. As a result, when the conventional high frequency apparatus is used in combination with bipolar electrodes, by which term is meant an electrode arrangement which is adapted to hold a tissue portion to be treated between a pair of electrodes, the spacing between the electrodes had to be reduced. Where a coagulation of the tissue over an extensive area is desired, a so-called monopolar electrode is used. The monopolar electrode is applied against a tissue portion to be treated, while the other electrode is held stationary against a distinct portion of the tissue. However, with a monopolar electrode, the coagulating action is not limited to the surface portion, but may proceed into the internal tissue portion, thereby disadvantageously coagulating a normal tissue.

SUMMARY OF THE INVENTION

It is an object of the invention to provide a high frequency apparatus for heat treatment of a biological tissue which completely eliminates the disadvantage of the prior art mentioned above, by energizing a pair of electrodes from the output of an amplifier which is connected with a high frequency oscillator and by maintaining the peak-to-peak value of the inter-electrode voltage at a low level on the order of 250 to 600 volts.

With the apparatus of the invention, the low peak-to-peak value of the inter-electrode voltage prevents the occurrence of a discharge between one of the electrodes and the tissue as the resistance of the tissue increases during the energization, thus preventing a localized increase in the potential gradient adjacent to one electrode and assuring a uniform coagulation of the entire tissue across the electrodes. With this arrangement, the current passes through the near surface portion of the tissue without influence in the inner tissue portion, thus achieving a coagulation to the intended extent. The constant voltage characteristic of the apparatus causes a reduction in the current flow through the tissue as the electrical resistance of the tissue lying between the electrodes increases, thus preventing the coagulation of an unintended area.

DETAILED DESCRIPTION OF PREFERRED EMBODIMENTS

Figure 1:
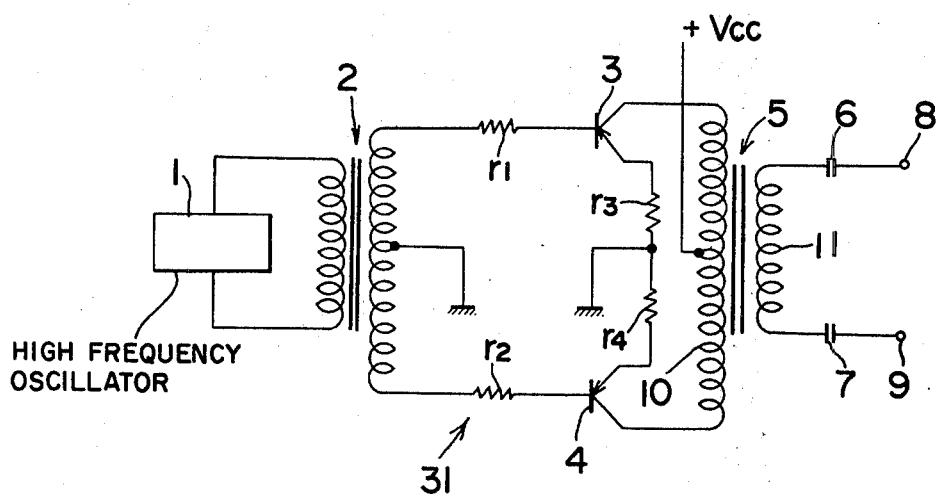
FIG. 1 is a circuit diagram of the high frequency apparatus for heat treatment of biological tissue constructed in accordance with the invention.
Figure 2:
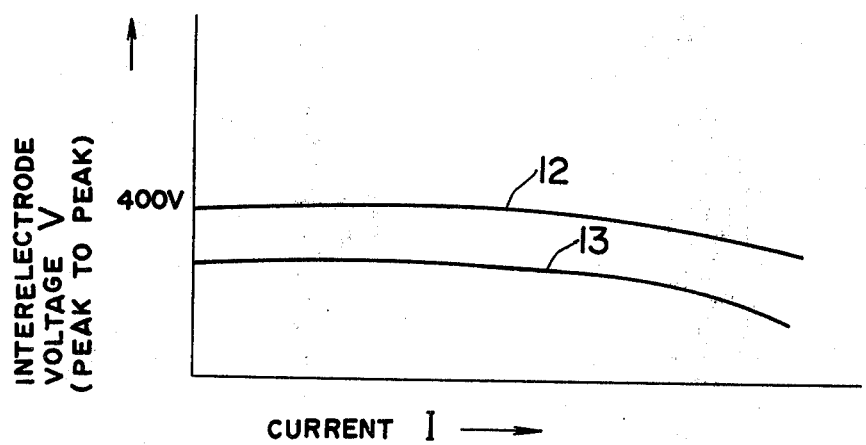
FIG. 2 graphically shows the output characteristic of the circuit shown in FIG. 1.

Referring to FIG. 1, the apparatus includes a high frequency oscillator 1 which is designed to produce an oscillation of 500 kHZ. The output of the oscillator 1 is fed through a transformer 2 to a push-pull amplifier 31 comprising a pair of transistors 3 and 4. The output of the amplifier 31 is supplied to a pair of electrodes 8 and 9 through another transformer 5 and through a pair of capacitors 6, 7. In accordance with the invention, it is desirable that the turns ratio of the primary winding 10 to the secondary winding 11 of the transformer 5 be chosen 1:1 or 2:1. The amplifier 31 is configured so that a constant voltage characteristic as indicated by solid line curves 12, 13 in FIG. 2 can be established with a voltage across the electrodes 8, 9 of a value from about 250 to about 600 volts, peak-to-peak. In a practical embodiment, a peak-to-peak value of about 400 volts is established across the electrodes for a 500 kHZ output of the oscillator 1 by choosing base resistors r1, r2 of 5 ohms, emitter resistors r3, r4 of 1 ohm and capacitors 6, 7 of 2000 pF. The tap on the primary winding of the transformer 5 is connected with a voltage source +Vcc of nearly 200 volts.

Figure 3:
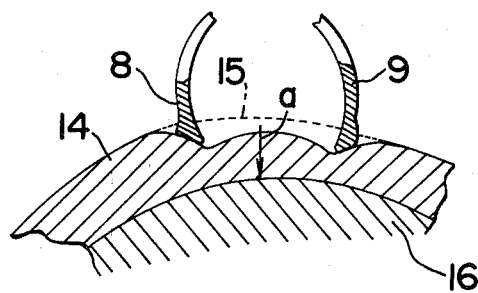
FIG. 3 is a schematic cross section of a biological tissue which is being coagulated by the apparatus of the invention.

With the apparatus of the invention, the low inter-electrode voltage prevents a discharge across one of the electrodes and the tissue if the electrical resistance of the tissue increases during the energization. As a consequence, no unbalanced increase in the potential gradient of one electrode relative to the other occurs, with the consequence that the degree of coagulation of the tissue is nearly uniform in both regions adjacent to the electrodes 8, 9. Because the high frequency current is used for energization, its passage is confined to the near surface region 15 of the tissue which region is successfully coagulated as shown in FIG. 3, while avoiding an inward progress of the coagulation as suggested by an arrow *a*, thus preserving a normal tissue portion 16. The electrical resistance presented across the electrodes 8, 9 increases as the coagulation proceeds, but the constant voltage characteristic reduces the coagulating current flow, thus effectively preventing an excessive coagulation. The coagulation is effective to fix the affected portion of the tissue and to stop the hemorrhage. An excision can be achieved by localized coagulation.

It is possible to have an adjustable output from the oscillator 1 by connecting a variable resistor therewith.

Figure 4:
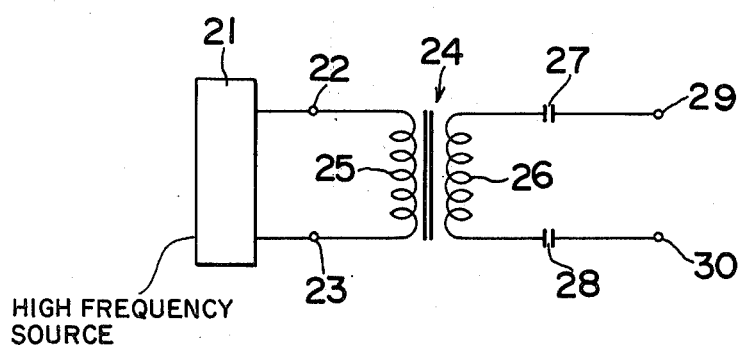
FIG. 4 is a schematic diagram of a conventional radioknife to which the invention is applied.

FIG. 4 shows another embodiment of the invention in which a high frequency source 21 of a conventional radioknife, which includes the amplifier 31, has its output terminals 22, 23 connected across a primary winding 25 of an impedance translating transformer 24, the secondary winding 26 of which is connected through capacitors 27, 28 with a pair of electrodes 29, 30. In the present embodiment, the turns ratio *n*:1 of the transformer 24 depends on the terminal voltage of the source 21 but the peak-to-peak value of the voltage across the electrodes 29, 30 is established below about 600 volts, preferably below about 400 volts.

What is claimed is:

1. A high frequency apparatus for heat treatment of a biological tissue, said apparatus comprising:

a high frequency oscillator;

amplifier means having its input connected to the output of said oscillator and having first and second bipolar outputs;

a pair of bipolar electrodes adapted to bear against a biological tissue at spaced points;

impedance transformation means for coupling the first and second outputs of said amplifier means to respective ones of said bipolar electrodes;

said amplifier means including means for generating a high frequency voltage for application to said bipolar electrodes wherein the peak-to-peak value of the voltage is in the range from 250 to 600 volts to cause a flow of high frequency current through that portion of the tissue extending between said electrodes to produce Joule's heat in accordance with an electrical resistance presented by the tissue to thereby treat the tissue with the Joule's heat whereby the low peak-to-peak voltage range prevents the occurrence of a discharge between either electrode and the tissue adjacent thereto due to any increase in tissue resistance, said amplifier means further including means for maintaining said peak-to-peak voltage constant so that any increase in tissue resistance causes a reduction in current flow through the tissue thereby preventing coagulation of those portions of the tissue not intended for treatment.

2. A high frequency apparatus according to claim 1 in which the amplifier means comprises a push-pull amplifier circuit.

3. A high frequency apparatus according to claim 1, wherein said impedance means comprises a transformer interposed between the outputs of said amplifier means and the bipolar electrodes and having a turns ratio of nearly 2:1 between its primary and secondary windings.

4. The apparatus of claim 1 wherein the peak-to-peak voltage range lies between 250 and 400 volts.

* * * * *